United States Patent [19]

D'Amico

[11] 4,227,915
[45] Oct. 14, 1980

[54] N-SUBSTITUTED OXOBENZOTHIAZOLINE AND OXOBENZOXAZOLINE DERIVATIVES AND THEIR USE AS PLANT GROWTH REGULANTS

[75] Inventor: John J. D'Amico, Olivette, Mo.

[73] Assignee: Monsanto Company, St. Louis, Mo.

[21] Appl. No.: 907,233

[22] Filed: May 18, 1978

[51] Int. Cl.² .............................................. A01N 9/12
[52] U.S. Cl. ........................................ 71/90; 71/73;
71/76; 71/77; 71/78; 71/88; 71/95; 260/245.5;
544/135; 544/137; 546/198; 548/171; 548/221
[58] Field of Search .................... 71/90, 88, 76, 100;
260/304 R, 307, 302 R

[56]  References Cited
U.S. PATENT DOCUMENTS

| 3,050,526 | 8/1962 | Lo ........................................ 260/304 |
| 3,069,429 | 12/1962 | Godson et al. .......................... 71/90 |
| 3,439,018 | 4/1969 | Brookes et al. ......................... 71/100 |
| 3,661,921 | 5/1972 | Umio .................................. 260/304 R |
| 3,668,213 | 6/1972 | Jamison ................................. 260/304 |
| 3,839,349 | 10/1974 | Wagner et al. ............................ 71/90 |
| 3,847,971 | 11/1974 | Koenig et al. ........................... 71/100 |
| 3,923,709 | 12/1975 | Worley .................................... 71/90 |
| 3,957,809 | 5/1976 | Hardy et al. ....................... 260/302 R |
| 3,993,468 | 11/1976 | D'Amico ................................. 71/90 |
| 4,022,607 | 5/1977 | Jackson .................................. 71/90 |
| 4,049,419 | 9/1977 | D'Amico ................................. 71/90 |
| 4,075,216 | 2/1978 | D'Amico ................................. 71/90 |
| 4,130,413 | 12/1978 | Handte et al. ........................... 71/90 |

FOREIGN PATENT DOCUMENTS 43-21378  9/1968 Japan ......................................... 71/90

OTHER PUBLICATIONS

Zinner et al., "Benzazoles XXIX 2-Oxo-3-, etc.," (1975), CA83, No. 114267m (1975).
Husain, "Search for Potent Anthelmintics etc., " (1974), CA82, No. 156159n (1975).

Primary Examiner—Glennon H. Hollrah
Attorney, Agent, or Firm—Patricia A. Coburn; Donald W. Peterson

[57] ABSTRACT

The present invention relates to compounds of the formula

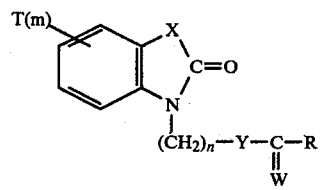

wherein
X, Y and W represent independently oxygen or sulfur;
T represents lower alkyl, lower alkoxy, halo, $CF_3$ or $NO_2$;
m is an integer of from 0 to 2;
n is an integer of from 1 to 3; and
R is selected from the group consisting of

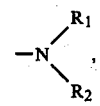

morpholino, pyrrolidyl, pyrrolidyl substituted by from 1 to 2 lower alkyl or lower alkoxy moieties and

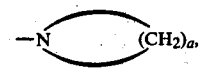

where a is an integer of from 5 to 8 inclusive;
$R_1$ represents lower alkyl, lower alkenyl, benzyl, phenyl or phenyl substituted by from 1 to 3 lower alkyl, lower alkoxy, lower alkenyl, $CF_3$ or $NO_2$ moieties;
$R_2$ represents hydrogen, lower alkyl or lower alkenyl moieties, with the proviso that when X is oxygen, $R_1$ and $R_2$ cannot equal methyl. The invention also relates to the use of said compounds in a method of regulating leguminous plant growth as well as to plant growth regulant compositions.

5 Claims, No Drawings

N-SUBSTITUTED OXOBENZOTHIAZOLINE AND OXOBENZOXAZOLINE DERIVATIVES AND THEIR USE AS PLANT GROWTH REGULANTS

BACKGROUND OF THE INVENTION

This invention relates to new N-substituted oxobenzothiazolines and oxobenzoxazolines and to their use in a method of regulating leguminous plant growth as well as to plant growth regulant compositions. New compounds which are useful in regulating plants have become increasingly important as the rapidly increasing world population continues to greatly increase the pressure on available world food supplies. An increase in food production through increased land utilization is not a viable solution to this problem because, although more land can be put into production than is now being cultivated, much of that land is marginal and may, in order to be productive, require substantial inputs of water and fossil fuel energy, which are themselves diminishing resources. As a result, the use of chemicals to produce yield increases through the physiological manipulation of the crop plant offers an important means of increasing crop yield.

It is presently known that certain benzothiazyl compounds possess herbicidal activity. U.S. Pat. No. 3,069,429 discloses the use of certain 4-halogeno-2-oxobenzothiazolin-3-yl acetic acids and their derivatives, such as salts, esters, amides, etc., to kill weeds. U.S. Pat. No. 3,839,349 discloses the use of certain N-substituted benzothiazolines useful as insecticides, fungicides and herbicides. None of these patents, however, disclose the use of the specific N-substituted oxobenzothiazolines or oxobenzoxazolines useful in accordance with the present invention to regulate the growth of plants.

It is further known that certain benzothiazyl compounds possess plant growth regulating activities. For example, Japanese Pat. No. 73/10182 discloses the use of certain N-substituted 2-oxo-3-benzothiazoline compounds as grafting agents for tree root growth. U.S. Pat. No. 3,993,468 and U.S. Pat. No. 4,049,419 disclose the use of certain benzothiazolines as plant growth regulants. Co-pending applications of D'Amico, Ser. No. 861,476 and Ser. No. 861,479, both filed Feb. 16, 1977, disclose N-amides and N-hydrazides of 2-benzothiazoline which are useful as plant growth regulants. However, none of the foregoing disclose the use of the specific novel oxobenzothiazolines or oxobenzoxazolines described by the present invention.

DESCRIPTION OF THE INVENTION

The invention relates to a new class of chemical compounds and their use as plant growth regulants. More specifically, the invention relates to novel N-substituted oxobenzothiazoline and oxobenzoxazoline derivatives useful in regulating the growth of leguminous plants.

N-substituted oxobenzothiazolines and oxobenzoxazolines useful in accordance with this invention are represented by the formula

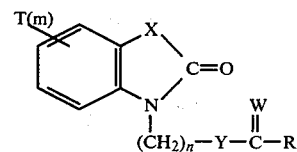

wherein:

X, Y and W represent independently oxygen or sulfur; T represents lower alkyl, lower alkoxy, halo, $CF_3$ or $NO_2$; m is an integer of from 0 to 2; n is an integer of from 1 to 3; and R is selected from the group consisting of

morpholino, pyrrolidyl, pyrrolidyl substituted by from 1 to 2 lower alkyl and lower alkoxy moieties and

where a is an integer of from 5 to 8 inclusive; $R_1$ represents lower alkyl, lower alkenyl, benzyl, phenyl or phenyl substituted by from 1 to 3 lower alkyl, lower alkoxy, lower alkenyl, $CF_3$ or $NO_2$ moieties; $R_2$ represents hydrogen, lower alkyl or lower alkenyl moieties; with the proviso that when X is oxygen, $R_1$ and $R_2$ cannot equal methyl.

In the description of the novel N-substituted oxobenzothiazoline and oxobenzoxazoline derivatives useful as plant growth regulants according to this invention, the following embodiments are intended for the various groups. The term lower alkyl includes those members including straight chain and branched chain, having from 1 to 5 carbon atoms, inclusive, for example, methyl, ethyl, n-propyl, isopropyl, n-butyl, sec-butyl, tert-butyl, n-pentyl, isopentyl, and the like. The term lower alkenyl are those straight or branched chain radicals, having from 2 to 5 carbon atoms and preferably from 3 to 5 carbon atoms and exemplified by 2-propenyl, 1-methyl-2-propenyl, 2-methyl-2-propenyl, 2-butenyl, 1-methyl-2-butenyl, 2-methyl-2-butenyl, 3-butenyl, 1-methyl-3-butenyl or 2-methyl-3-butenyl and the like. The term lower alkoxy preferably includes those members, including straight chain and branched chain, having from 1 to 5 carbon atoms, inclusive, for example, methoxy, ethoxy, n-propoxy, isopropoxy, n-butoxy, sec-butoxy, tert-butoxy, n-butoxy, isopentoxy and the like. Where the term "halo" or halogen is used herein, it is understood to mean chlorine, bromine, fluorine and iodine. Where the term "morpholino" is used herein it is understood to mean a radical having the structure

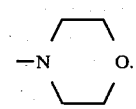

The term "pyrrolidyl" is understood to mean a radical of the structure

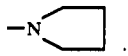

The radical represented by the formula

means a nitrogen-containing heterocycle containing 5 to 8 carbon atoms, e.g., piperadino, hexamethyleneimino, heptamethyleneimino, octamethyleneimino, and the like.

One preferred sub-class of chemicals employed as leguminous plant growth regulants are those wherein R is

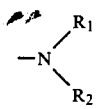

and wherein X, T, m, n, Y, W, $R_1$ and $R_2$ have the values previously stated. Especially preferred are those compounds wherein R is

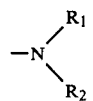

and X is sulfur.

Typical compounds within the scope of this invention include, but are not limited to the following: 2-(2-oxobenzothiazolin-3-yl)ethyl methyl carbamate; 2-(2-oxabenzothiazolin-3-yl)ethyl carbanilate; 2-(2-oxobenzothiazolin-3-yl) ethyl dimethylcarbamate; 2-(2-oxobenzoxazolin-3-yl) ethyl dimethylcarbamate; 3-(2-oxobenzothiazolin-3-yl)propyl dipropylthiolcarbamate; 3-(6-ethoxy-2-oxobenzothiazolin-3-yl)propyl dipropylthiolcarbamate; 3-(2-oxobenzothiazolin-3-yl)propyl dipropylthiolcarbamate; 3-(2-oxobenzothiazolin-3-yl)propyl dimethylthiolcarbamate; 3-(2-oxobenzothiazolin-3-yl)propyl diisopropylthiolcarbamate; 3-(5-chloro-2-oxobenzothiazolin-3-yl)propyl dimethylthiolcarbamate; 2-(5-chloro-2-oxobenzothiazolin-3-yl)ethyl dipropylthiolcarbamate; 2-(2-oxobenzothiazolin-3-yl)ethyl dipropylthiolcarbamate; 3-(5-chloro-2-oxobenzothiazolin-3-yl)-propyl diisopropylthiolcarbamate; 2-(2-oxobenzothiazolin-3-yl)ethyl diisopropylthiolcarbamate; 2-(5-chloro-2-oxobenzothiazolin-3-yl)ethyl diisopropylthiolcarbamate; 2-(2-oxobenzothiazolin-3-yl)ethyl diethylthiolcarbamate; 2-(5-chloro-2-oxobenzothiazolin-3-yl)ethyl diethylthiolcarbamate; 3-(2-oxobenzothiazolin-3-yl)propyl diethylthiolcarbamate; 3-(5-chloro-2-oxobenzothiazolin-3-yl)propyl diethylthiolcarbamate; 2-(5-chloro-2-oxobenzothiazolin-3-yl)ethyl dimethylthiolcarbamate; 2-(2-oxobenzothiazolin-3-yl)ethyl dimethylthiolcarbamate; 3-(2-oxobenzothiazolin-3-yl)propyl N-benzyl-N-ethylthiolcarbamate; 3-(2-oxobenzothiazolin-3-yl)propyl 2,5-dimethylpyrrolidylcarbothiolate; (2-oxobenzothiazolin-3-yl) methyl diisopropylthiolcarbamate; (2-oxobenzothiazolin-3-yl) methyl dimethyldithiolcarbamate; (2-oxobenzothiazolin-3-yl) methyl diethyldithiolcarbamate; (2-oxobenzoxazolin-3-yl)methyl dimethyldithiocarbamate; (2-oxobenzoxazolin-3-yl)methyl diethyldithiocarbamate; (2-oxobenzothiazolin-3-yl)methyl pyrrolidylcarbodithiolate; (2-oxobenzoxazolin-3-yl)methyl pyrrolidylcarbodithiolate; (2-oxobenzoxazolin-3-yl)methyl 4-morpholinocarbodithiolate; 3-(2-oxobenzothiazolin-3-yl) propyl diethylthionocarbamate; 2-(2-oxobenzothiazolin-3-yl) ethyl diethylthionocarbamate; 2-(2-oxobenzothiazolin-3-yl) ethyl dimethylthionocarbamate; 2-(2-oxobenzothiazolin-3-yl) ethyl dipropylthionocarbamate; 3-(2-oxobenzothiazolin-3-yl) propyl dimethylthionocarbamate; 2-(2-oxobenzothiazolin-3-yl) ethyl dibutylthionocarbamate; 2-(2-oxobenzothiazolin-3-yl) ethyl 4-morpholinocarbothionate; 3-(2-oxobenzothiazolin-3-yl)propyl dibutylthionocarbamate; 3-(2-oxobenzothiazolin-3-yl)propyl dipropylthionocarbamate; 2-(2-oxobenzothiazolin-3-yl)ethyl 4-morpholinocarbothionate; 2-(6-bromo-2-oxobenzothiazolin-3-yl)ethyl dimethylthionocarbamate; 2-(6-ethoxy-2-oxobenzothiazolin-3-yl)ethyl dimethylthionocarbamate; 3-(5-chloro-2-oxobenzoxazolin-3-yl)propyl diethylthionocarbamate; 3-(2-oxobenzothiazolin-3-yl)propyl N-methylcarbanilate.

The term "active ingredient" is used herein to describe the novel N-substituted oxobenzothiazolines and N-substituted oxobenzoxazolines of the formula previously described. Various methods can be used to prepare the N-substituted oxobenzothiazoline and oxobenzoxazoline compounds found to be useful in regulating the growth of leguminous plants. The following examples describe these methods and the active compounds formed thereby in greater detail.

EXAMPLE 1

Benzothiazolinone and benzoxazolinone intermediates are prepared according to the following reaction:

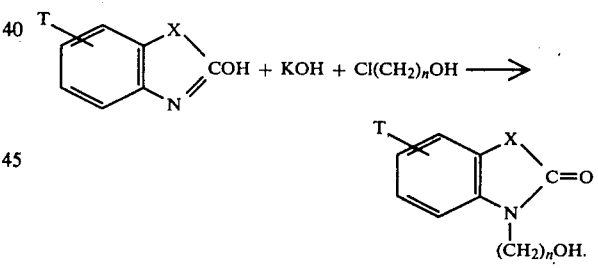

To a stirred solution containing 1 mol of the appropriate 2-hydroxybenzothiazole or benzoxazole, 66 g (1.0 mol) of 85% potassium hydroxide, 300–500 ml of water, 1.1 mol of 2-chloroethanol or 3-chloropropanol was added in one portion. The stirred reaction mixture was heated at 90°–100° C. for 5 hours and at 25°–30° C. for 18 hours. For Compounds A-C of Table I the stirred reaction mixture was cooled to 5° C. After stirring at 0°–10° C. for 30 minutes, the products were collected by filtration, washed with 200 ml of water and air-dried at 25°–30° C. For Compounds D and E of Table I, the stirred reaction mixtures were extracted with 500–600 ml of ethyl ether and chloroform, respectively. The separated solvent layers were washed with water until neutral and dried over sodium sulfate. The solvents (ethyl ether or chloroform) were removed in vacuo at a maximum temperature of 80°–90° C. at 1–2 mm. The data are summarized in Table I.

TABLE I

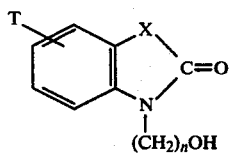

| Intermediate Compound | T | X | n | MP °C. | % Yield | % C Calc'd | % C Found | % H Calc'd | % H Found | % N Calc'd | % N Found | % S Calc'd | % S Found |
|---|---|---|---|---|---|---|---|---|---|---|---|---|---|
| A | H | S | 2 | 94–5[a] | 98 | — | — | — | — | 7.17 | 7.11 | 16.42 | 16.12 |
| B | H | O | 2 | 110–1[b] | 95 | 60.32 | 60.50 | 5.06 | 5.11 | 7.81 | 7.75 | — | — |
| C | 6-Br | S | 2 | 133–4[a] | 96 | 39.43 | 39.34 | 2.94 | 2.72 | 5.11 | 5.19 | 11.70 | 12.08 |
| D | 6-OC$_2$H$_5$ | S | 2 | Visc. Liquid | 66 | 55.21 | 54.74 | 5.48 | 5.29 | 5.85 | 5.95 | 13.40 | 13.58 |
| E | H | S | 3 | Visc. liquid | 94 | — | — | — | — | 6.69 | 6.72 | 15.32 | 15.22 |

[a] Recrystallization from toluene
[b] Recrystallization from isopropyl alcohol

The intermediates prepared according to Example 1 and described in Table I are utilized to prepare various of the active compounds of the present invention as illustrated by the following examples The products were collected by filtration and air-dried at 25°–30° C. The data are summarized in Table II.

TABLE II

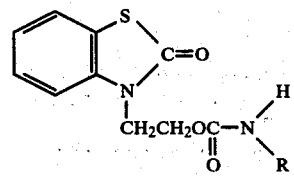

| Compound No. | R | MP °C. | Yield | % N Calc'd | % N Found | % S Calc'd | % S Found |
|---|---|---|---|---|---|---|---|
| 1 | —CH$_3$ | 107–8[a] | 95 | 11.10 | 11.05 | 12.71 | 12.90 |
| 2 | —C$_6$H$_5$ | 122–23[a] | 86 | 8.91 | 8.95 | 10.20 | 10.49 |

[a] Recrystallization from ethyl alcohol

EXAMPLE 2

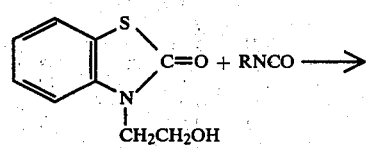

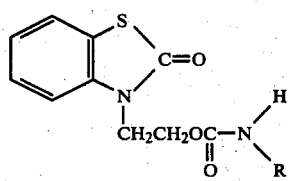

To a stirred charge containing 19.5 g (0.1 mol) of 3-(2-hydroxyethyl)-2-benzothiazolinone, 100 ml of ethyl acetate and 1 ml of triethylamine, 0.1 mol of the appropriate isocyanate was added in one portion. The stirred reaction mixture was heated at reflux for 6 hours and at 25°–30° C. for 18 hours. After cooling to 5° C., the reaction mixture was stirred at 0°–10° C. for 1 hour.

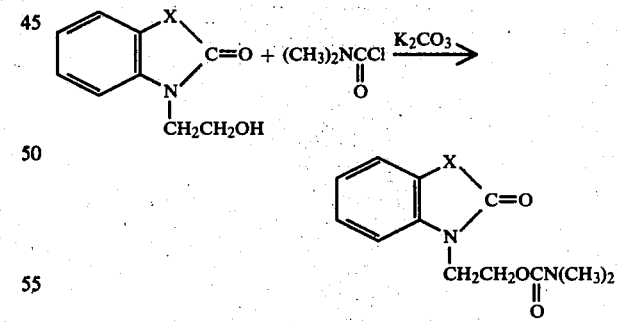

To a stirred slurry containing 0.2 mol of 3-(2-hydroxyethyl)-2-benzothiazolinone or 3-(2-hydroxyethyl)-2-benzoxazolinone, 28 g (0.2 mol) of potassium carbonate and 200 ml of heptane 26.6 g, (0.25 mol) of dimethylcarbamoyl chloride was added in one portion. The stirred reaction mixture was heated at reflux for 7 hours and at 25°–30° C. for 18 hours. After the addition of 800 ml of water, stirring was continued for 1 hour. The solids were collected by filtration, washed with water until neutral and air-dried at 25°–30° C. The data are summarized in Table III.

TABLE III

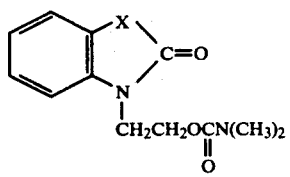

| Compound No. | X | MP °C. | Yield | % C Calc'd | % C Found | % H Calc'd | % H Found | % N Calc'd | % N Found |
|---|---|---|---|---|---|---|---|---|---|
| 3 | S | 74–5[a] | 77 | 54.12 | 54.32 | 5.30 | 5.25 | 10.52 | 10.43 |
| 4 | O | 82–3[b] | 72 | 57.59 | 57.62 | 5.64 | 5.65 | 11.20 | 10.92 |

[a] Recrystallization from heptane - isopropyl alcohol
[b] Recrystallization from isopropyl alcohol

EXAMPLE 4

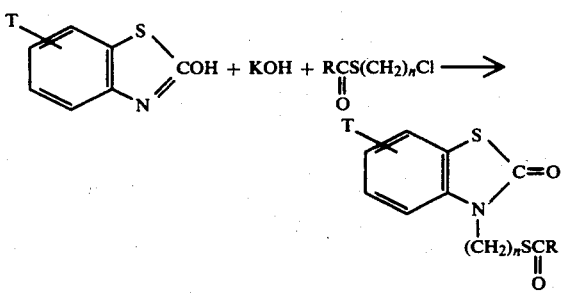

To a stirred charge containing 0.11 mol of 5-chloro or 6-ethoxy, or unsubstituted 2-hydroxybenzothiazole, 7.3 g (0.11 mol) of 85% potassium hydroxide, and 200 ml of DMF, 0.1 mol of the appropriate 2-chloroethyl or 3-chloropropyl disubstituted thiolcarbamate was added in one portion. The stirred reaction mixture was heated at 90°–100° C. for 24 hours. After cooling to 25° C., 500 ml of water and 600 ml of ethyl ether were added and stirring continued at 25°–30° C. for 15 minutes. The ether was removed in vacuo at maximum temperature at 25°–30° C. or 80°–90° C. at 1–2 mm. The data are summarized in Table IV.

TABLE IV

| Compound No. | T | n | R | MP °C. | % Yield | % Cl Calc'd | % Cl Found | % N Calc'd | % N Found | % S Calc'd | % S Found |
|---|---|---|---|---|---|---|---|---|---|---|---|
| 5 | 5-Cl | 3 | —N(C₃H₇)₂ | a | 90 | — | — | 7.24 | 7.92 | 16.57 | 16.77 |
| 6 | 6-OC₂H₅ | 3 | —N(C₃H₇)₂ | a | 80 | — | — | 7.06 | 7.34 | 16.17 | 15.70 |
| 7 | H | 3 | —N(C₃H₇)₂ | a | 90 | — | — | 7.95 | 8.06 | 18.19 | 17.98 |
| 8 | H | 3 | —N(CH₃)₂ | a | 74 | — | — | 9.45 | 9.50 | 21.64 | 21.29 |
| 9 | H | 3 | —N(CH(CH₃)₂)₂ | a | 88 | — | — | 7.95 | 8..48 | 18.19 | 17.80 |
| 10 | 5-Cl | 3 | —N(CH₃)₂ | a | 83 | 10.72 | 11.34 | 8.47 | 8.29 | — | — |
| 11 | 5-Cl | 2 | —N(C₃H₇)₂ | a | 81 | — | — | 7.51 | 7.64 | — | — |
| 12 | H | 2 | —N(C₃H₇)₂ | a | 89 | — | — | 8.28 | 8.34 | 18.95 | 18.98 |
| 13 | 5-Cl | 3 | —N(CH(CH₃)₂)₂ | 88–90[b] | 44 | 9.16 | 8.50 | 7.24 | 7.11 | 16.57 | 17.16 |
| 14 | H | 2 | —N(CH(CH₃)₂)₂ | a | 84 | — | — | 8.28 | 8.74 | 18.95 | 18.68 |
| 15 | 5-Cl | 2 | —N(CH(CH₃)₂)₂ | a | 81 | — | — | 7.51 | 7.88 | — | — |
| 16 | H | 2 | —N(C₂H₅)₂ | a | 71 | — | — | 9.02 | 8.84 | — | — |
| 17 | 5-Cl | 2 | —N(C₂H₅)₂ | a | 73 | — | — | 8.12 | 8.09 | — | — |
| 18 | H | 3 | —N(C₂H₅)₂ | a | 78 | — | — | 8.63 | 8.86 | 19.77 | 19.42 |
| 19 | 5-Cl | 3 | —N(C₂H₅)₂ | a | 78 | 9.88 | 9.42 | 7.81 | 8.21 | — | — |
| 20 | 5-Cl | 2 | —N(CH₃)₂ | a | 70 | 11.19 | 10.70 | 8.84 | 8.45 | — | — |
| 21 | H | 2 | —N(CH₃)₂ | 82–4[b] | 50 | — | — | 9.92 | 9.48 | 22.71 | 23.20 |
| 22 | H | 3 | —N(CH₂C₆H₅)(C₂H₅) | a | 85 | — | — | 7.25 | 7.05 | 16.59 | 16.87 |
| 23 | H | 3 | —N(pyrrolidine with 2,5-diCH₃) | a | 86 | — | — | 7.99 | 7.81 | 18.30 | 18.40 |

[a] Very visc. amber liquid
[b] Ether removed in vacuo at maximum 30° C. at 1–2 mm and the product was air-dried at 25°–30° C. on a porous plate

EXAMPLE 5

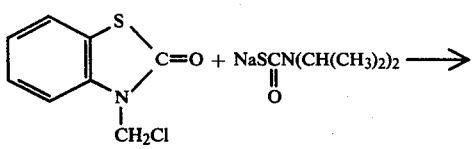

To a stirred charge containing 15 g (0.15 mol) of diisopropylamine, 8 g (0.1 mol) of 50% sodium hydroxide and 50 ml of water, 7.8 g (0.15 mol) of 85% carbonyl sulfide was added at 0°–10° C. over a 15 minute period. To this stirred mixture, 19.6 g (0.1 mol) of 3-chloromethyl-2-benzothiazolinone (U.S. Pat. No. 3,050,526) and 100 ml of tetrahydrofuran were added in one portion. The reaction mixture was stirred at 0°–20° C. for the first four hours and at 25°–30° C. for two days. After the addition of 800 g of ice water stirring was continued at 0°–10° C. for 30 minutes. The solid was collected by filtration, washed with water until neutral to litmus and air-dried at 25°–30° C. The product (2-oxobenzothiazolin-3-yl) methyl diisopropylthiolcarbamate (Compound No. 24) was obtained in 86% yield. After recrystallization from heptane/isopropyl alcohol, Compound No. 24 melted at 118°–120° C.

Anal. Calc'd for $C_{15}H_{20}N_2O_2S_2$: C, 55,43; H, 6.21; N, 8.63; S, 19.76 Found: C, 55.48; H, 6.24; N, 8.62; S, 19.83.

EXAMPLE 6

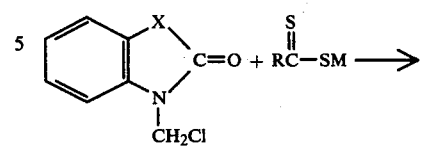

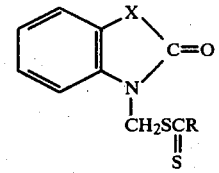

To a stirred charge containing 0.11 mol of the appropriate sodium or triethylamine salt of disubstituted dithiocarbamic acid in 200 ml of acetone, 0.1 mol of 3-chloromethyl-2-benzothiazolinone (U.S. Pat. No. 3,050,526) or 3-chloromethyl-2-benzoxazolinone (Zinner, Ber. 89, 2135) was added in one portion. The stirred reaction mixture was heated at reflux for 24 hours. After cooling to 5° C., 800 g of ice water was added and stirring continued at 0°–10° C. for 30 minutes. The products were collected by filtration, washed with water until neutral to litmus and air-dried at 25°–30° C. The data are summarized in Table V.

TABLE V

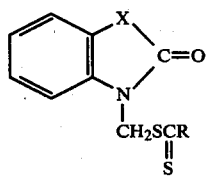

| Compound No. | X | R | M | MP °C. | % Yield | % C Calc'd | % C Found | % H Calc'd | % H Found | % N Calc'd | % N Found | % S Calc'd | % S Found |
|---|---|---|---|---|---|---|---|---|---|---|---|---|---|
| 25 | S | —N(CH₃)₂ | Na . 2H₂O | 135–6[a] | 95 | 46.45 | 46.46 | 4.25 | 4.28 | 9.85 | 9.90 | 33.82 | 33.75 |
| 26 | S | —N(C₂H₅)₂ | H . N(C₂H₅)₃ | 112–3[b] | 99 | 49.97 | 49.85 | 5.16 | 5.17 | 8.97 | 8.95 | 30.78 | 30.73 |
| 27 | O | —N(CH₃)₂ | Na . 2H₂O | 163–4[a] | 95 | 49.23 | 49.95 | 4.51 | 4.66 | 10.44 | 10.39 | 23.90 | 23.76 |
| 28 | O | —N(C₂H₅)₂ | Na . 3H₂O | 88–9[b] | 99 | 52.68 | 52.68 | 5.44 | 5.45 | 9.45 | 9.43 | 21.63 | 21.61 |
| 29 | S | 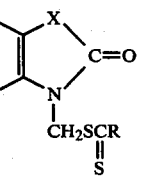 | H . N(C₂H₅)₃ | 165–7[a] | 97 | 50.29 | 50.22 | 4.55 | 4.58 | 9.02 | 9.04 | 30.98 | 30.98 |
| 30 | O | —N⟨ | H . N(C₂H₅)₃ | 148–9[a] | 95 | 53.04 | 53.12 | 4.79 | 4.81 | 9.52 | 9.53 | 21.78 | 21.75 |
| 31 | O | —N⟨O | H . N(C₂H₅)₃ | 140–1[a] | 97 | 50.30 | 50.96 | 4.55 | 4.67 | 9.03 | 8.97 | — | — |

[a]Recrystallization from ethyl acetate
[b]Recrystallization from isopropyl alcohol A group of the novel active compounds were prepared using xanthate intermediates. The preparation of the novel xanthates is illustrated in Example 7.

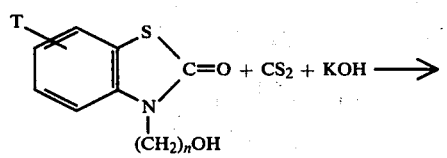

-continued

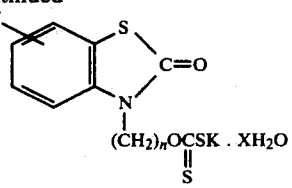

To a stirred charge containing 0.25 mol of the appropriate alcohol (Table I) in 500 ml of carbon disulfide, 16.5 g (0.25 mol) of potassium hydroxide was added in small portions at 20°-25° C. over a 10 minute period. After stirring at 25°-30° C. for 24 hours, 600 ml of ethyl ether was added. The products were collected by filtration and air-dried at 25°-30° C. The data are summarized in Table VI.

-continued

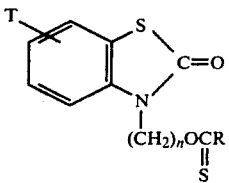

To a stirred solution containing 20.9 g (0.15 mol) of bromoacetic acid in 250 ml of water, 12 g (0.08 mol) of potassium carbonate was added in small portions until pH=8 was obtained. To this stirred solution 0.15 mol of the appropriate xanthate (Table VI) was added in one portion and stirring continued at 25°-30° C. for 1.5 hours. The appropriate disubstituted amine was added in one portion and stirring continued at 25°-30° C. for 24 hours. For all solid products, 200 g of ice water was added and the stirred reaction mixture held at 0°-10° C. for 30 minutes. The solids were collected by filtration, washed with water until neutral to litmus and air-dried at 25°-30° C. For all liquids, the stirred reaction mixture was extracted with 500 ml of ethyl ether. The separated ether layer was washed with water until neutral to litmus and dried over sodium sulfate. The ether was removed in vacuo at maximum temperature of 80°-90° C. at 1-2 mm. The data are summarized in Table VII.

TABLE VI

| Intermediate Compound | T | n | % Yield | X | % C Calc'd | % C Found | % H Calc'd | % H Found | % N Calc'd | % N Found | % S Calc'd | % S Found |
|---|---|---|---|---|---|---|---|---|---|---|---|---|
| F | H | 2 | 99 | Zero | — | — | — | — | 4.52 | 4.47 | — | — |
| G | H | 3 | 89 | 2 | — | — | — | — | 3.89 | 3.76 | 26.75 | 26.10 |
| H | 6-Br | 2 | 93 | Zero | 30.93 | 30.10 | 1.82 | 2.03 | 3.61 | 3.75 | — | — |
| I | 6-OC$_2$H$_5$ | 2 | 95 | Zero | — | — | — | — | 3.96 | 3.69 | — | — |

EXAMPLE 8

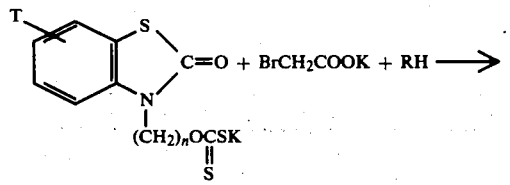 + BrCH$_2$COOK + RH ⟶

TABLE VII

| Compound No. | T | n | R | MP °C. | % Yield | % C Calc'd | % C Found | % H Calc'd | % H Found | % N Calc'd | % N Found | % S Calc'd | % S Found |
|---|---|---|---|---|---|---|---|---|---|---|---|---|---|
| 32 | H | 3 | —N(C$_2$H$_5$)$_2$ | Visc. Liquid | 52 | — | — | — | — | 8.63 | 8.00 | 19.76 | 19.29 |
| 33 | H | 2 | —N(C$_2$H$_5$)$_2$ | 89–90[a] | 47 | — | — | — | — | 9.02 | 8.96 | 20.65 | 20.64 |
| 34 | H | 2 | —N(CH$_3$)$_2$ | 126–7[a] | 52 | — | — | — | — | 9.92 | 9.69 | 22.71 | 22.59 |
| 35 | H | 2 | —N(C$_3$H$_7$)$_2$ | Visc. Liquid | 75 | — | — | — | — | 8.28 | 8.31 | 18.95 | 19.16 |
| 36 | H | 3 | —N(CH$_3$)$_2$ | 114–5[a] | 98 | 52.67 | 53.00 | 5.44 | 5.51 | 9.45 | 9.54 | 21.63 | 21.82 |
| 37 | H | 2 | —N(C$_4$H$_9$)$_2$ | Visc. Liquid | 71 | — | — | — | — | 7.64 | 7.58 | 17.50 | 17.70 |
| 38 | H | 2 | —N(CH$_2$CH$_2$)$_2$O | 147–8[b] | 70 | 51.83 | 51.65 | 4.97 | 4.83 | 8.64 | 8.38 | 19.77 | 19.96 |
| 39 | H | 3 | —N(C$_4$H$_9$)$_2$ | Visc. Liquid | 86 | — | — | — | — | 7.36 | 7.12 | 16.85 | 16.94 |

TABLE VII-continued

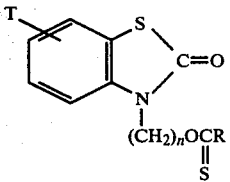

| Compound No. | T | n | R | MP °C. | % Yield | % C Calc'd | % C Found | % H Calc'd | % H Found | % N Calc'd | % N Found | % S Calc'd | % S Found |
|---|---|---|---|---|---|---|---|---|---|---|---|---|---|
| 40 | H | 3 | —N(C₃H₇)₂ | Visc. Liquid | 70 | — | — | — | — | 7.95 | 8.12 | 18.19 | 18.77 |
| 41 | H | 3 | —N⟨(CH₂)₄⟩O (morpholino) | 122-3[b] | 91 | — | — | — | — | 8.28 | 8.08 | 18.95 | 19.21 |
| 42 | 6-Br | 2 | —N(CH₃)₂ | 131-2[b] | 76 | 38.89 | 39.79 | 3.63 | 3.66 | 7.75 | 7.68 | 17.75 | 17.66 |
| 43 | 6-OC₂H₅ | 2 | —N(CH₃)₂ | 121-2[a] | 49 | 51.51 | 51.24 | 5.56 | 5.57 | 8.58 | 8.50 | 19.64 | 19.83 |

[a]Recrystallization from isopropyl alcohol
[b]Recrystallization from ethyl acetate

EXAMPLE 9

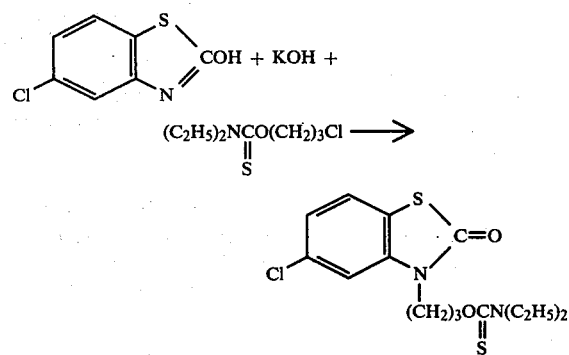

To a stirred charge containing 20.4 g (0.11 mol) of 5-chloro-2-hydroxybenzothiazole, 7.3 g (0.11 mol) of 85% potassium hydroxide and 200 ml of DMF, 21 g (0.1 mol) of 3-chloropropyl diethylthionocarbamate was added in one portion. The stirred reaction mixture was heated at 90°–100° C. for 24 hours. After cooling to 25° C., 500 ml of water and 600 ml of ethyl ether were added and stirring continued at 25°–30° C. for 15 minutes. The separated ether layer was washed with water until neutral to litmus and dried over sodium sulfate. The ether was removed in vacuo at maximum temperature of 80°–90° C. at 1-2 mm. The product, an amber viscous liquid, 3-(5-chloro-2-oxobenzothiazolin-3-yl) propyl diethylthionocarbamate (Compound No. 44) was obtained in 81% yield.

Anal. Calc'd for C₁₅H₉ClN₂O₂S₂: N, 7.81; S, 17.87 Found: N, 8.38; S, 17.80

EXAMPLE 10

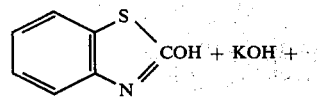

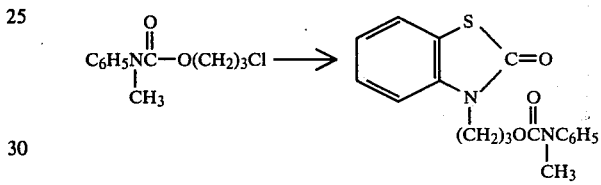

To a stirred charge containing 15.1 g (0.1 mol) of 2-hydroxybenzothiazole, 6.6 g (0.1 mol) of 85% potassium hydroxide and 150 ml of DMF, 22.8 g (0.1 mol) of 3-chloropropyl N-methylcarbanilate was added in one portion. The stirred reaction mixture was heated at 90°–100° C. for 24 hours. After cooling to 25° C., 500 ml of water and 600 ml of ethyl ether were added and stirring continued at 25°–30° C. for 15 minutes. The separated ether layer was washed with water until neutral to litmus and dried over sodium sulfate. The ether was removed in vacuo at maximum temperature of 80°–90° C. at 1-2 mm. The product, 3-(2-oxobenzothiazolin-3-yl)propyl N-methyl carbanilate (Compound No. 45) was obtained as a dark amber viscous liquid in 82% yield.

Anal. Calc'd for C₁₈H₁₈N₂O₃S: N, 8.18; S, 9.36 Found: N, 8.38; S, 9.42

Compounds of the formula described above have been found to produce a variety of plant growth regulatory responses when applied to leguminous crop plants, for example, soybean (Glycine max). The terms "plant growth regulant effect", plant growth regulation" or words to that effect, are used in this specification and in the claims to mean the causation by the chemicals of the present invention, of a variety of plant responses which achieve a promotion, inhibition or modification of any plant physiological or morphological process. It should additionally be recognized that various plant responses may also result from a combination or sequence of both physiological and morphological factors.

The plant growth regulant effects which may be produced in leguminous plants using the method of the present invention are probably most readily observable as changes in the size, shape, color or texture of the treated plant or any of its parts. Similarly, changes in the quantity of the plant fruit or flowers are also quite apparent from visual inspection. The above changes may be characterized as an acceleration or retardation of plant growth, stature reduction, leaf or canopy alteration, increased branching, tillering, terminal inhibition, increased flowering or fruit set, increased root growth, axillary but development or inhibition, delayed budding, defoliation, desiccation, delayed senescence, prolongated dormancy, increased cold hardiness, delayed or accelerated ripening, and the like.

Although many of the above modifications are per se desirable, it is most often the ultimate effect of such modifications on the economic factor that is of primary significance. For example, reducing the physical size of each plant in a field permits the growing of more plants per unit area and leads to more efficient use of crop land. Many plants of reduced stature are more tolerant of drought and cold temperatures and are more resistant to pest infestations and to lodging. Reduction in the maturation rate on portions of a crop permits an extended harvest period at peak yield and more efficient use of subsequent crop processing equipment. Suppression of vegetative growth at the appropriate stage of the plant's development may result in increased energy available for utilization in reproductive development so that, for example, more fruit or larger fruit is formed.

Increased plant dry matter accumulation is a valuable plant growth regulant response which can occur in conjunction with morphological changes or can be the sole plant growth response detected. Increased dry matter accumulation is the physically measurable manifestation of increased plant photosynthetic activity. Most plants capture no more than 1 to 3 percent of the solar energy they receive. Present knowledge suggests that it is theoretically possible to increase this rate to approximately twelve percent. Enhancement of photosynthesis at the appropriate stage of the plant's growth and development may enable the plant to fix more carbon dioxide resulting in the production of increased amounts of carbohydrate, amino acids, etc., which could be available for utilization in the plant's reproductive activities, leading to increased crop yields.

It is to be understood that the regulation of desirable crop plants in accordance with the instant invention does not include the total inhibition or the killing of such plants. Although phytotoxic amounts of the materials disclosed herein might be employed to exert a herbicidal (killing) action, it is contemplated here to employ only plant regulating amounts of such materials in order to modify the normal sequential development of the treated plant to agricultural maturity. The application of a plant regulating amount may be applied to plants in sequence at various stages of the plants' development to obtain various desirable responses. As may be expected, and as is apparent to those skilled in the art, such plant regulating amounts will vary, not only with the material selected, but also with the modifying effect desired, the species of plant and its stage of development, the plant growth medium and whether a permanent or transitory effect is sought.

In accordance with this invention it has been found that desirable modification of leguminous crop plants is achieved by applying the above-described plant regulants to the "plant" or plant "habitat". The term "plant" is understood herein to include the seeds, emerging seedlings, roots, stems, leaves, flowers, fruits or other plant parts. The term "habitat" is understood herein to mean the environment of the plant such as the plant growing medium, e.g., the soil.

In the practice of the invention, the active ingredient can be used alone or in combination with a material referred to in the art as an adjuvant in either liquid or solid form. To prepare plant growth regulating compositions, the active ingredient is admixed with an adjuvant including diluents, extenders, carriers and conditioning agents to provide compositions in the form of finely-divided particulate solids, granules, pellets, wettable powders, dusts, solutions and aqueous dispersions or emulsions. Thus, the active ingredient can be used with an adjuvant such as a finely-divided particulate solid, a solvent liquid of organic origin, water, a wetting agent, dispersing agent or emulsifying agent or any suitable combination of these.

Illustrative finely-divided solid carriers and extenders which are useful in plant growth regulating compositions of this invention include the talcs, clays, pumice, silica, diatomaceous earth, quartz, Fullers earth, sulfur, powdered cork, powdered wood, walnut flour, chalk, tobacco dust, charcoal and the like. Typical liquid diluents include Stoddard solvent, acetone, alcohols, glycols, ethyl acetate, benzene and the like. The plant growth regulating compositions of this invention, particularly liquids and wettable powders, usually contain one or more surface-active agents in amounts sufficient to render a given composition readily dispersible in water or in oil. The term "surface-active agent" is understood to include wetting agents, dispersing agents, suspending agents and emulsifying agents. Such surface-active agents are well-known and reference is made to U.S. Pat. No. 2,547,724, Columns 3 and 4, for detailed examples of the same.

Generally, the active ingredients are applied in the form of a composition containing one or more adjuvants which aid in the application of a uniform distribution of the active ingredient. The application of liquid and particulate solid compositions of the active ingredient can be carried out by conventional techniques utilizing for example, spreaders, power dusters, boom and hand sprayers and spray dusters. The compositions can also be applied from airplanes as a dust or spray. Should the application of the plant growth composition to the plant growth medium be desired, this is accomplished by incorporating the compositions in the soil or other media in the area where modifications of the plants is desired.

Compositions of this invention generally contain from about 5 to 95 parts active ingredient, about 1 to 50 parts surface active agent and about 5 to 94 parts solvent, all parts being by weight based on the total weight of the composition.

In selecting the appropriate rate of application of the active ingredient, it will be recognized that precise rates will also be dependent upon the mode of application, such as soil incorporation, band application, pre-plant seed treatment and various other factors known to those skilled in the art. In foliar treatment for the regulation of plant growth, the active ingredients are applied in amounts of from about 0.05 to about 10 pounds per acre. Preferred are foliar applications of from 0.05 to 5 pounds of the active ingredient per acre. In application to the soil habitat of germinant seeds, emerging seedlings and established vegetation for the regulation of plant growth, the active ingredients are applied in amounts of from 0.1 to about 10 pounds per acre or more. The application to the soil of from 0.1 to about 5 pounds of active ingredient per acre is preferred. Foliar application to plants beginning to blossom are preferred over other types of applications.

In accordance with the practice of the invention, several plant growth regulating compositions were formulated utilizing several of the novel N-substituted oxobenzothiazolines or oxobenzoxazoline as the active ingredient. The compositions were formulated so that they could be applied at a rate the equivalent of 200 gallons per acre (306 liters per hectare). Table VIII illustrates the formulation of the composition for several application rates of active ingredient. The formulation of the composition for other rates of application is well within the skill of the art. In each formulation, the stock solution utilized is 1% of the active ingredient dissolved in acetone.

TABLE VIII

| RATE Lbs/Acre | (kilos hectare) | ml of 1% Stock Solution | ml Acetone | ml of 0.39% TWEEN 20 In Water As Surfactant |
|---|---|---|---|---|
| 6.0 | (6.72) | 2.0 | — | 3.6 |
| 5.0 | (5.60) | 2.0 | 1.0 | 3.7 |
| 3.0 | (3.36) | 1.0 | 1.0 | 3.6 |
| 2.5 | (2.80) | 1.0 | 2.0 | 3.7 |
| 1.2 | (1.34) | 0.4 | 1.6 | 3.6 |
| 1.0 | (1.12) | 0.4 | 2.6 | 3.7 |
| 0.5 | (0.560) | 0.2 | 2.8 | 3.7 |
| 0.3 | (0.336) | 0.1 | 1.9 | 3.6 |

When several of the novel oxobenzothiazoline and oxobenzoxazoline active compounds were formulated in accordance with Table VIII, the formulations exhibited unexpected plant growth regulating properties as illustrated by the test set forth in Example 11.

EXAMPLE 11

A number of soybean plants, variety Corsoy, are grown from seeds in aluminum pans in a greenhouse for a period of approximately one week to the primary leaf stage. The plants are thinned to three uniform plants in each pan and the height of each plant in the pan is measured to the terminal bud and the average height is noted. One pan containing three soybean plants is used for each chemical treatment and three pans are not treated and used as a control. An aqueous composition of the active ingredient is then applied to the pan of growing plants by overhead spray at the desired rate. The treated pans, along with the control pans, are maintained in a greenhouse and watered from below on a sand bench and fertilized with a uniform portion of a water-soluble balanced fertilizer.

Two weeks after application of the chemical the average height of the soybean plants in the treated pan is again measured as above and the difference in the average height before and two weeks after application represent the increased in the development of the treated plants. This development in growth of the treated plants is compared to the average increase in growth of the plants in the control pans during the same period of time. A variation of 25% or more in the development of at least two-thirds of the treated plants when compared to the development of the control plants demonstrates that the chemical is an effective plant regulant. Thus, a chemical is considered active when the treated plants manifest a decrease in growth of at least 25% less than that of the control plants, i.e., stature reduction or an increase in growth in excess of 25% of that of the control plants, i.e., growth stimulation.

Table IX summarizes the results for the observations made in accordance with Example 11 when the novel N-substituted oxobenzothiazoline or N-substituted oxobenzoxaline compounds of the present invention are utilized as the active ingredient at several application rates.

TABLE IX

| Compound No. | Lbs Acre | Kilos Hectare | Response |
|---|---|---|---|
| 3 | 6.0 | 6.72 | Stature reduction, axillary bud development, leaf distortion, slight leaf burn |
|   | 3.0 | 3.36 | Leaf alteration, leaf distortion, slight leaf burn |
| 4 | 6.0 | 6.72 | Stature reduction, leaf distortion, leaf inhibition, slight leaf burn |
|   | 3.0 | 3.36 | Axillary bud development, leaf distortion, slight leaf burn |
|   | 1.2 | 1.34 | Leaf distortion, leaf inhibition |
| 32 | 6.0 | 6.72 | No response noted |
| 33 | 6.0 | 6.72 | Axillary bud development, leaf distortion |
|   | *2.5 | 2.80 | Leaf distortion, chlorosis |
|   | *1.25 | 1.40 | Leaf distortion |
|   | *.50 | .56 | No response noted |
|   | *.50 | .56 | No response noted |
|   | *.25 | .28 | No response noted |
| 34 | 6.0 | 6.72 | Leaf distortion, inhibition of apical development, thick leaf texture |
|   | 6.0 | 6.72 | Leaf distortion, inhibition of apical development |
|   | 3.0 | 3.36 | Leaf distortion, inhibition of apical development |
|   | 1.2 | 1.34 | No response noted |
| 35 | 6.0 | 6.72 | Leaf distortion, inhibition of apical development |
|   | 6.0 | 6.72 | Leaf distortion, inhibition of apical development, thick leaf texture |
|   | 3.0 | 3.36 | Leaf distortion, inhibition of apical development |
|   | 1.2 | 1.34 | Stature reduction, leaf distortion |
| 36 | 6.0 | 6.72 | Axillary bud development |
| 37 | 6.0 | 6.72 | Axillary bud development, inhibition of apical development, leaf distortion |
|   | 6.0 | 6.72 | Stature reduction, inhibition of apical development, leaf distortion |
|   | 3.0 | 3.36 | Inhibition of apical development, thick leaf texture, leaf distortion |
|   | 1.2 | 1.34 | Leaf distortion |

TABLE IX-continued

| Compound No. | RATE Lbs Acre | RATE Kilos Hectare | Response |
|---|---|---|---|
| 38 | 6.0 | 6.72 | No response noted |
| 39 | 6.0 | 6.72 | Altered canopy, chlorosis |
|  | 6.0 | 6.72 | Chlorosis, slight leaf burn |
|  | 3.0 | 3.36 | Chlorosis, slight leaf burn |
|  | 1.2 | 1.34 | Chlorosis, slight leaf burn |
| 40 | 6.0 | 6.72 | Leaf distortion |
| 41 | 6.0 | 6.72 | Slight leaf burn |

*Test procedure followed varied from Example 11. There was 1 plant/pot and the plant was treated with test chemical at the 3rd leaf stage.

Further advantages of this invention are shown in Example 12.

EXAMPLE 12

A number of soybean plants, variety Williams, are grown from seeds in plastic pots in the greenhouse for a period of one week at which time the plants are thinned to one plant per pot. When the second trifoliate leaf (three weeks) was fully expanded, the plants were treated with a solution of the active ingredient in acetone and water. Aqueous Tween 20 is used as a surfactant.

When the fifth trifoliate leaf (four to five weeks) was fully expanded, the treated plants were compared with the non-treated control plants and the observations recorded.

Table X below summarizes the results and observations made in accordance with the above procedure.

TABLE X

| Compound No. | RATE Lbs Acre | RATE Kilos Hectare | % Dry* Weight | Response |
|---|---|---|---|---|
| 1 | 0.1 | 0.14 | 93 | No response noted |
|  | 0.5 | 0.56 | 98 | Leaf alteration, slight leaf burn |
|  | 2.5 | 2.80 | 77 | Leaf distortion, altered canopy, moderate leaf burn |
| 3 | 0.1 | 0.14 | 93 | No response noted |
|  | 0.5 | 0.56 | 104 | Leaf alteration |
|  | 2.5 | 2.80 | 80 | Leaf alteration, altered canopy, leaf distortion, moderate leaf burn |
| 4 | 0.1 | 0.14 | 89 | No response noted |
|  | 0.5 | 0.56 | 80 | Leaf alteration, leaf distortion, slight leaf burn |
|  | 2.5 | 2.80 | 74 | Altered canopy, leaf alteration, leaf distortion, axillary bud inhibition, moderate leaf burn |
| 5 | 0.1 | 0.14 | 78 | Leaf alteration |
|  | 0.5 | 0.56 | 75 | Stature reduction, altered canopy, leaf distortion, leaf inhibition, slight leaf burn |
|  | 2.5 | 2.80 | 74 | Stature reduction, altered canopy, leaf distortion, leaf inhibition, axillary bud inhibition, slight leaf burn |
| 6 | 0.1 | 0.14 | 111 | No response noted |
|  | 0.5 | 0.56 | 122* | Leaf alteration, axillary bud inhibition |
|  | 2.5 | 2.80 | 94 | Stature reduction, leaf distortion, leaf alteration, altered canopy, axillary bud inhibition, slight leaf burn |
| 7 | 0.1 | 0.14 | 101 | Leaf distortion, leaf alteration, slight leaf burn |
|  | 0.5 | 0.56 | 71 | Leaf distortion, leaf alteration, altered canopy, axillary bud inhibition, slight leaf burn |
|  | 2.5 | 2.80 | 71 | Stature reduction, leaf distortion, leaf alteration, leaf inhibition, altered canopy, moderate leaf burn |
| 9 | 0.1 | 0.14 | 103 | Leaf alteration |
|  | 0.5 | 0.56 | 82 | Leaf distortion, leaf alteration, axillary bud inhibition, slight leaf burn |
|  | 2.5 | 2.80 | 78 | Stature reduction, leaf distortion, leaf alteration, leaf inhibition, axillary bud inhibition, moderate leaf burn |
| 11 | 0.1 | 0.14 | 86 | No response noted |
|  | 0.5 | 0.56 | 90 | No response noted |
|  | 2.5 | 2.80 | 92 | Leaf alteration, leaf inhibition, slight leaf burn |
| 12 | 0.1 | 0.14 | 112 | No response noted |
|  | 0.5 | 0.56 | 86 | Leaf distortion, slight leaf burn |
|  | 2.5 | 2.80 | 82 | Stature reduction, leaf distortion, leaf alteration, altered canopy, slight leaf burn |
| 14 | 0.1 | 0.14 | 99 | No response noted |
|  | 0.5 | 0.56 | 89 | Leaf alteration, leaf distortion, slight |

*Calculated as percent of control

TABLE X-continued

| Compound No. | RATE Lbs Acre | RATE Kilos Hectare | % Dry* Weight | Response |
|---|---|---|---|---|
| | | | | leaf burn |
| | 2.5 | 2.80 | 83 | Leaf alteration, leaf distortion, altered canopy, axillary bud inhibition, chlorosis, slight leaf burn |
| 15 | 0.1 | 0.14 | 94 | No response noted |
| | 0.5 | 0.56 | 87 | Leaf alteration, leaf distortion, slight leaf burn |
| | 2.5 | 2.80 | 88 | Leaf alteration, leaf distortion, slight leaf burn |
| 16 | 0.1 | 0.14 | 103 | No response noted |
| | 0.5 | 0.56 | 93 | Leaf alteration, leaf distortion, leaf inhibition, altered canopy, axillary bud inhibition, slight leaf burn |
| | 2.5 | 2.80 | 79 | Stature reduction, altered canopy, leaf alteration, leaf distortion, leaf inhibition, moderate leaf burn |
| 18 | 0.1 | 0.14 | 94 | Leaf alteration |
| | 0.5 | 0.56 | 91 | Leaf alteration, leaf distortion, slight leaf burn |
| | 2.5 | 2.80 | 81 | Leaf alteration, leaf distortion, leaf inhibition, altered canopy, moderate leaf burn |
| 19 | 0.1 | 0.14 | 90 | No response noted |
| | 0.5 | 0.56 | 93 | No response noted |
| | 2.5 | 2.80 | 73 | Leaf alteration, leaf distortion, slight leaf burn |
| 20 | 0.1 | 0.14 | 89 | No response noted |
| | 0.5 | 0.56 | 88 | No response noted |
| | 2.5 | 2.80 | 55 | Leaf alteration, leaf distortion, slight leaf burn |
| 21 | 0.1 | 0.14 | 102 | No response noted |
| | 0.5 | 0.56 | 99 | Leaf alteration |
| | 2.5 | 2.80 | 85 | Altered canopy, leaf alteration, leaf distortion, slight leaf burn |
| 23 | 0.1 | 0.14 | 93 | No response noted |
| | 0.5 | 0.56 | 72 | Leaf alteration |
| | 2.5 | 2.80 | 67 | Leaf alteration, leaf distortion, leaf inhibition, altered canopy, axillary bud inhibition, slight leaf burn |
| 32 | 0.1 | 0.14 | 107 | No response noted |
| | 0.5 | 0.56 | 89 | Leaf alteration, leaf inhibition, leaf distortion, altered canopy, slight leaf burn |
| | 2.5 | 2.80 | 63 | Stature reduction, inhibition of apical development, altered canopy, leaf distortion leaf inhibition, moderate leaf burn |
| 33 | 0.1 | 0.14 | 104 | Slight leaf burn |
| | 0.5 | 0.56 | 92 | Leaf alteration, altered canopy, inhibition of apical development, slight leaf burn |
| | 2.5 | 2.80 | 70 | Stature reduction, inhibition of apical development, altered canopy, leaf distortion, stem distortion, moderate leaf burn |
| 34 | 0.1 | 0.14 | 120 | Leaf alteration |
| | 0.5 | 0.56 | 99 | Leaf alteration |
| | 2.5 | 2.80 | 67 | Stature reduction, altered canopy, leaf alteration, leaf distortion, stem distortion |
| 35 | 0.1 | 0.14 | 70 | No response noted |
| | 0.5 | 0.56 | 72 | Leaf alteration |
| | 2.5 | 2.80 | 67 | Altered canopy, leaf alteration, leaf distortion, chlorosis, slight leaf burn |
| 36 | 0.1 | 0.14 | 135* | Slight leaf burn |
| | 0.5 | 0.56 | 116* | Altered canopy, leaf distortion, chlorosis, slight leaf burn |
| | 2.5 | 2.80 | 99 | Altered canopy, leaf distortion, chlorosis, moderate leaf burn |
| 38 | 0.1 | 0.14 | 86 | No response noted |
| | 0.5 | 0.56 | 87 | Altered canopy, leaf alteration, slight leaf burn |
| | 2.5 | 2.80 | 69 | Stature reduction, altered canopy, inhibition of apical development, leaf alteration, stem distortion, moderate leaf burn |
| 41 | 0.1 | 0.14 | 106 | No response noted |
| | 0.5 | 0.56 | 104 | Chlorosis, slight leaf burn |
| | 2.5 | 2.80 | 88 | Leaf distortion, chlorosis, slight leaf burn |

*Did not confirm on retest.

Compound Numbers 34, 35 and 37 were further tested according to the procedure described in Example 13.

EXAMPLE 13

Individual soybean plants, variety Corsoy, are grown from seed in 6-inch pots containing a good grade of top soil. Two pots of 4 week old plants (3-4 trifoliate stage) and two pots of 6-week old plants (5-6 trifoliate stage) are used for each application of the chemical. An overhead spray of an aqueous composition of the chemical is applied to the pots at the rate indicated in Table XI. Two to four sets of plants which received no chemical application are included and serve as controls. All of the pots are maintained under good growing conditions and are watered and fertilized with a uniform amount of a water-soluble balanced fertilizer. Two weeks after the application of the chemical, the growth responses of the treated plants are compared with that of the control plants. The total height of the plant is measured to the tip of the terminal bud. A variation of 15 percent in the average total height of the treated plants, when compared to the average total height of the control plants, demonstrates that the chemical is an effective plant growth regulator. These observations are repeated at four weeks after chemical application as a further evaluation of plant regulatory activity. The observations made on 4 week and 6-week-old plants, at 2 and 4 weeks form a composite evaluation. Observations made utilizing the test procedure of Example 13 are summarized in Table XI.

TABLE XI

| Compound No. | Lbs Acre | Kilos Hectare | Response |
|---|---|---|---|
| 34 | 1.0 | 1.12 | No response noted |
|  | 5.0 | 5.60 | No response noted |
| 35 | 1.0 | 1.12 | No response noted |
|  | 2.5 | 2.80 | No response noted |
|  | 5.0 | 5.60 | No response noted |
| 37 | 1.0 | 1.12 | No response noted |
|  | 2.5 | 2.80 | Enhanced pod set |
|  | 5.0 | 5.60 | Enhanced pod set |

The N-substituted oxobenzothiazoline and N-substituted oxobenzoxazoline compounds described herein exhibit unexpected properties when used to regulate the growth of leguminous crop plants, especially soybean (Glycine max).

Although this invention has been described with respect to specific modifications, the details thereof are not to be construed as limitations, for it will be apparent that various equivalents, changes and modifications may be resorted to without departing from the spirit and scope thereof and it is understood that such equivalent embodiments are intended to be included herein.

What is claimed:

1. A method of regulating the natural growth and development of leguminous plants which method comprises applying to said leguminous plants or their habitat an effective plant growth regulating amount of a compound of the formula

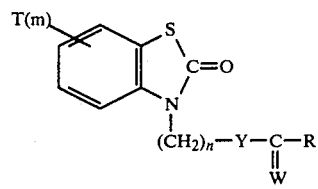

wherein Y and W represent independently oxygen or sulfur; T represents lower alkyl, lower alkoxy, $CF_3$ or $NO_2$; m is an integer of from 0 to 1; n is an integer of from 1 to 3; and R is selected from the group consisting of

morpholino, pyrrolidyl and pyrrolidyl substituted by from 1 to 2 lower alkyl, lower alkenyl or lower alkoxy moieties; $R_1$ represents lower alkyl, lower alkenyl, benzyl, phenyl or phenyl substituted by from 1 to 3 lower alkyl, lower alkoxy, lower alkenyl, $CF_3$ or $NO_2$ moieties; $R_2$ represents hydrogen, lower alkyl or lower alkenyl moieties.

2. A method according to claim 1 wherein R is

3. A method according to claim 2 wherein Y is sulfur.
4. A method according to claim 1 wherein Y is sulfur.
5. A method according to claim 1 wherein W is sulfur.